(12) United States Patent
Hyun et al.

(10) Patent No.: US 10,395,110 B2
(45) Date of Patent: Aug. 27, 2019

(54) IRIS SCANNING CAMERA MODULE AND MOBILE DEVICE INCLUDING THE SAME

(71) Applicant: SAMSUNG ELECTRO-MECHANICS CO., LTD., Suwon-si (KR)

(72) Inventors: Hae Seung Hyun, Suwon-si (KR); Soon Seok Kang, Suwon-si (KR); Ik Jin Jang, Suwon-si (KR); Jae Sun Lee, Suwon-si (KR); Dae Sik Kim, Suwon-si (KR)

(73) Assignee: Samsung Electro-Mechnics Co., Ltd., Suwon-si (KR)

( * ) Notice: Subject to any disclaimer, the term of this patent is extended or adjusted under 35 U.S.C. 154(b) by 56 days.

(21) Appl. No.: 15/607,910

(22) Filed: May 30, 2017

(65) Prior Publication Data
US 2018/0096204 A1    Apr. 5, 2018

(30) Foreign Application Priority Data

Oct. 4, 2016   (KR) .................. 10-2016-0127633
Feb. 23, 2017  (KR) .................. 10-2017-0023922

(51) Int. Cl.
*A61B 3/14*     (2006.01)
*G06K 9/00*     (2006.01)
(Continued)

(52) U.S. Cl.
CPC ........ *G06K 9/00604* (2013.01); *A61B 3/1216* (2013.01); *G06K 9/209* (2013.01);
(Continued)

(58) Field of Classification Search
CPC .......... G06K 9/00604; G06K 9/00617; G06K 9/2027; G06K 9/00201; G06K 9/00255;
(Continued)

(56) References Cited

U.S. PATENT DOCUMENTS

2008/0007623 A1    1/2008  Lee et al.
2009/0278048 A1    11/2009 Choe et al.
(Continued)

FOREIGN PATENT DOCUMENTS

JP    2016-174028 A    9/2016
KR    10-0809277 B1    3/2008
(Continued)

OTHER PUBLICATIONS

Korean Office Action dated Jan. 17, 2018, in corresponding Korean Application No. 10-2017-0023922 (7 pages in English, 6 pages in Korean).

*Primary Examiner* — Brandi N Thomas
(74) *Attorney, Agent, or Firm* — NSIP Law

(57) ABSTRACT

An iris scanning camera module includes a housing having an internal space, and a first lens module and a second lens module inside the internal space. The first lens module and the second lens module have optical axes parallel to each other. An image sensor is configured to convert light passing through the first lens module and the second lens module into an image. The image sensor is divided into a region including a color pixel array and as another region including a black-and-white pixel array. The color pixel array is aligned in an optical axis direction of the first lens module, and the black-and-white pixel array is aligned in an optical axis direction of the second lens module.

17 Claims, 6 Drawing Sheets

(51) Int. Cl.
*A61B 3/12* (2006.01)
*G06K 9/20* (2006.01)
*G06K 9/22* (2006.01)

(52) U.S. Cl.
CPC .............. *G06K 9/2018* (2013.01); *G06K 9/22* (2013.01); *G06K 9/00617* (2013.01); *G06K 9/2027* (2013.01)

(58) Field of Classification Search
CPC .............. G06K 9/00288; G06K 9/0061; G06K 9/00892; G06K 9/00906; G06K 9/2036; G06K 9/4652; G06K 9/4661; G06K 9/00597; G06K 9/2018; G06K 9/209; G06K 9/22; G02B 5/208; G02B 26/007; G02B 7/006; G02B 7/02; G02B 27/28; G02B 7/005
USPC ......... 351/200, 205, 206, 209–211, 221, 223
See application file for complete search history.

(56) References Cited

U.S. PATENT DOCUMENTS

| | | | |
|---|---|---|---|
| 2012/0257090 A1 | 10/2012 | Sa et al. | |
| 2016/0127658 A1* | 5/2016 | Li | H04N 5/2254 348/78 |
| 2016/0377426 A1* | 12/2016 | Kim | G01C 3/08 348/135 |

FOREIGN PATENT DOCUMENTS

| | | |
|---|---|---|
| KR | 10-1262507 B1 | 5/2013 |
| KR | 10-2013-0090599 A | 8/2013 |
| KR | 10-1475464 B1 | 12/2014 |
| KR | 10-2015-0083224 A | 7/2015 |
| KR | 10-2016-0103541 A | 9/2016 |

* cited by examiner

IRIS SCANNING CAMERA MODULE AND MOBILE DEVICE INCLUDING THE SAME

CROSS-REFERENCE TO RELATED APPLICATION(S)

This application claims the benefit under 35 U.S.C. § 119(a) of Korean Patent Application Nos. 10-2016-0127633, filed on Oct. 4, 2016 and 10-2017-0023922, filed on Feb. 23, 2017 in the Korean Intellectual Property Office, the entire disclosures of which are incorporated herein by reference for all purposes.

BACKGROUND

1. Field

The following description relates to an iris scanning camera module and a mobile device including the same.

2. Description of Related Art

In general, portable electronic devices such as mobile phones, smartphones, and personal digital assistants (PDAs) are equipped with camera modules for capturing images as a standard component. More recently, camera modules for iris recognition have been used as a means of user authentication in portable electronic devices. In general, infrared light is used for iris recognition imaging, while visible light is used for general imaging. Thus, in order to perform both general imaging and iris recognition imaging, portable electronic devices are equipped with camera modules for iris recognition in addition to camera modules for general imaging. As a result, the amount of space occupied by camera modules in portable electronic devices is increased.

SUMMARY

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an iris scanning camera module includes a housing having an internal space, and a first lens module and a second lens module inside the internal space. The first lens module and the second lens module each have an optical axis. The optical axes are parallel to each other. The iris scanning camera module has an image sensor configured to convert light passing through the first lens module and the second lens module into an image. The image sensor is divided into a region including a color pixel array and another region including a black-and-white pixel array. The color pixel array is aligned in a direction of the optical axis of the first lens module, and the black-and-white pixel array is aligned in a direction of the optical axis of the second lens module.

The second lens module of the iris scanning camera module may accommodate an iris recognition camera. The optical axis of the second lens module can be aligned with the center of the black-and-white pixel array in the iris scanning camera module. The housing may have an optical filter disposed between the image sensor and the first and second lens modules.

The optical filter of the iris scanning camera module may be divided into an infrared blocking filter region and an infrared pass filter region. The infrared blocking filter region can be aligned with the color pixel array of the image sensor, and the infrared pass filter region can be aligned with the black-and-white pixel array of the image sensor. The optical filter of the iris scanning camera module may pass both infrared light and ultraviolet light.

The first lens module of the iris scanning camera module may have a structure in which at least two lenses are stacked. The number of stacked lenses of the first lens module can be equal to or greater than a number of stacked lenses of the second lens module. Stacked lenses provided in the first lens module and the second lens module may be integrated with each other or separated from each other.

A diameter of an effective area of the first lens module may be the same as a diameter of an effective area of the second lens module. A diameter of the effective area of the first lens module can be different from a diameter of the effective area of the second lens module.

In another general aspect, an iris scanning camera module includes a housing having an internal space, and a first lens module and a second lens module inside the internal space. The first lens module and the second lens module each have an optical axis. The optical axes are parallel to each other. The iris scanning camera module also includes an optical filter disposed between an image sensor and the first and second lens modules. The iris scanning camera module further includes the image sensor, which is configured to convert light passing through the first lens module and the second lens module into an image. The optical filter is divided into an infrared blocking filter region and an infrared pass filter region. The infrared blocking filter region is aligned with the optical axis of the first lens module, and the infrared pass filter region is aligned with the optical axis of the second lens module.

The image sensor of the iris scanning camera module may include a color pixel array. A portable electronic device may include a body having a camera module according to the above general aspects mounted therein. The body of the portable electronic device may have an infrared light source configured to emit infrared light.

Other features and aspects will be apparent from the following detailed description, the drawings, and the claims.

Figure 1:
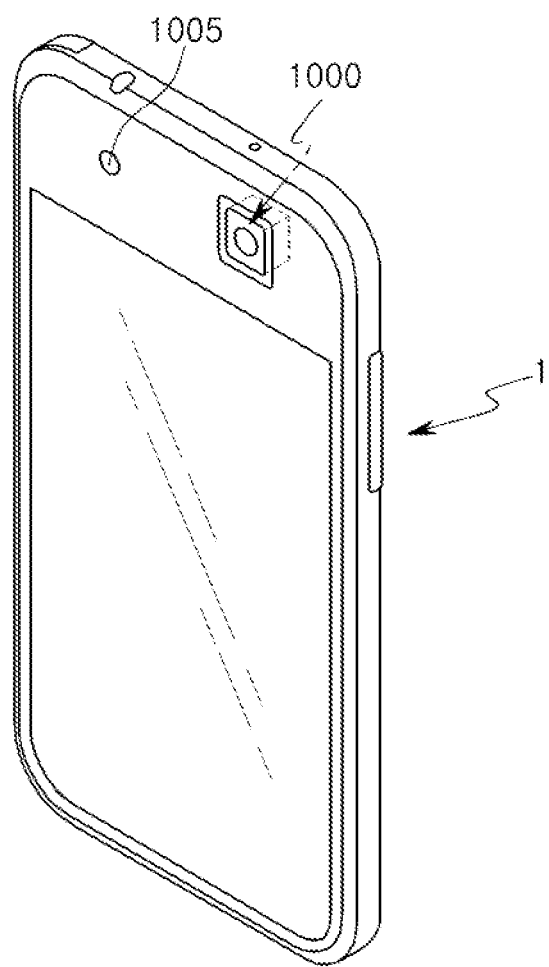
FIG. 1 is a perspective view of a portable electronic device having a camera module according to an example.

Throughout the drawings and the detailed description, the same reference numerals refer to the same elements, where applicable. The drawings may not be to scale, and the relative size, proportions, and depiction of elements in the drawings may be exaggerated for clarity, illustration, or convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure. The sequences of operations described herein are merely examples, and are not limited to those set forth herein, but may be changed as will be apparent after an understanding of the disclosure, with the exception of operations necessarily occurring in a certain order. Also, descriptions of functions and constructions that are well known may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure after an understanding of the application.

Throughout the specification, it will be understood that when an element, such as a layer, region or wafer (substrate), is referred to as being "on," "connected to," or "coupled to" another element, it can be directly "on," "connected to," or "coupled to" the other element, or other elements intervening therebetween may be present. In contrast, when an element is referred to as being "directly on," "directly connected to," or "directly coupled to" another element, there may be no elements or layers intervening therebetween. As used herein, the term "and/or" includes any and all combinations of one or more of the associated listed items.

The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Due to manufacturing techniques and/or tolerances, variations of the shapes shown in the drawings may occur. Thus, the examples described herein are not limited to the specific shapes shown in the drawings, but include changes in shape that occur during manufacturing.

Subsequently, examples are described in further detail with reference to the accompanying drawings. Examples provide an iris scanning camera module that may perform both general imaging and iris recognition imaging, using a single camera module.

FIG. 1 is a perspective view of a portable electronic device 1 according to an example. Referring to FIG. 1, the portable electronic device 1 according to an example has a camera module 1000 mounted therein. Examples of the portable electronic device 1 include a mobile communications terminal, a smartphone, and/or a tablet personal computer (PC).

As illustrated in FIG. 1, the camera module 1000 is mounted in the portable electronic device 1 to image a subject. In this example, the camera module 1000 includes both an iris recognition camera module and a general camera module. Accordingly, the portable electronic device 1 according to an example has an infrared light source 1005 for use by the iris recognition camera module. The infrared light source 1005 may be a light emitting diode (LED) light source. Further, the camera module 1000 may have functions such as auto focusing (hereinafter, referred to as "AF"), zooming, and optical image stabilizing (hereinafter, referred to as "OIS").

As will be described below, the camera module 1000, according to the example, has a first lens module 210 and a second lens module 220, and thus has first and second optical axes Z1 and Z2, respectively. The first lens module 210 is a camera lens module for general imaging, and the second lens module 220 is a camera lens module for iris recognition imaging.

Accordingly, the numbers of stacked lenses of the first and second lens modules 210 and 220 are different from each other, and the number of the stacked lenses of the second lens module 220 used for iris recognition is commonly less than that of the stacked lenses of the first lens module 210. In this example, the first and second lens modules 210 and 220 have the same number of stacked lenses in the structure of the camera module 1000, and thus a lens having no optical performance is provided in the second lens module 220, thereby reducing lens production costs.

The camera module 1000 according to this example has an AF or zoom function, and controls the AF or zoom function in a different manner, depending on whether the first lens module 210 or the second lens module 220 is used.

Figure 2:
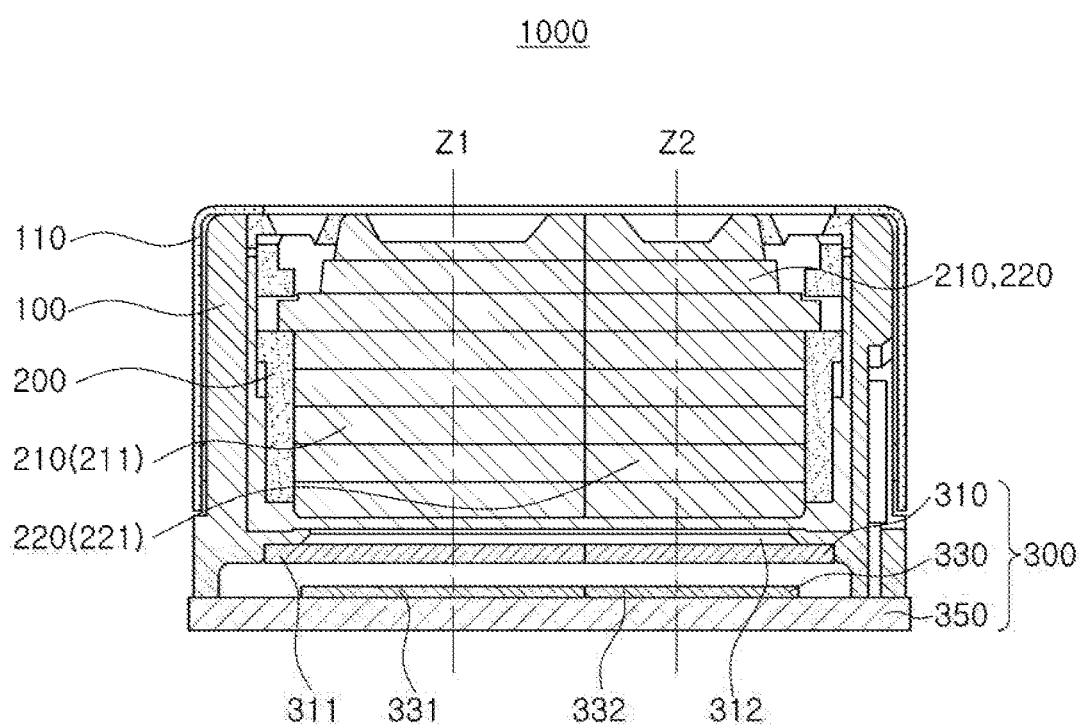
FIG. 2 is a cross-sectional view of a camera module according to an example.

FIG. 2 is a cross-sectional view of camera module 1000 according to the example. Referring to FIG. 2, the camera module 1000 includes housing 100, lens holder 200 disposed inside the housing 100, first lens module 210 and second lens module 220 disposed inside the lens holder 200. The camera module 1000 also includes an image sensor module 300, converting light incident through the first and second lens modules 210 and 220 into an electrical signal. The housing 100 has a case 110 covered on an upper portion thereof.

The lens holder 200 has a hollow shape to accommodate a plurality of lenses therein, and the lenses are mounted on the lens holder 200 on an optical axis thereof. The lenses may be directly provided in the lens holder 200, or a separate lens barrel (not illustrated) may be provided and then disposed in lens holder 200 while having lenses stacked therein.

The lenses according to this example have a dual lens structure including the first and second lens modules 210 and 220. In other words, the lenses are sequentially stacked inside a single lens holder 200, and may be dual lenses, each having an optical axis Z1 of the first lens module 210 and an optical axis Z2 of the second lens module 220 to thus have two optical systems.

Figure 9:
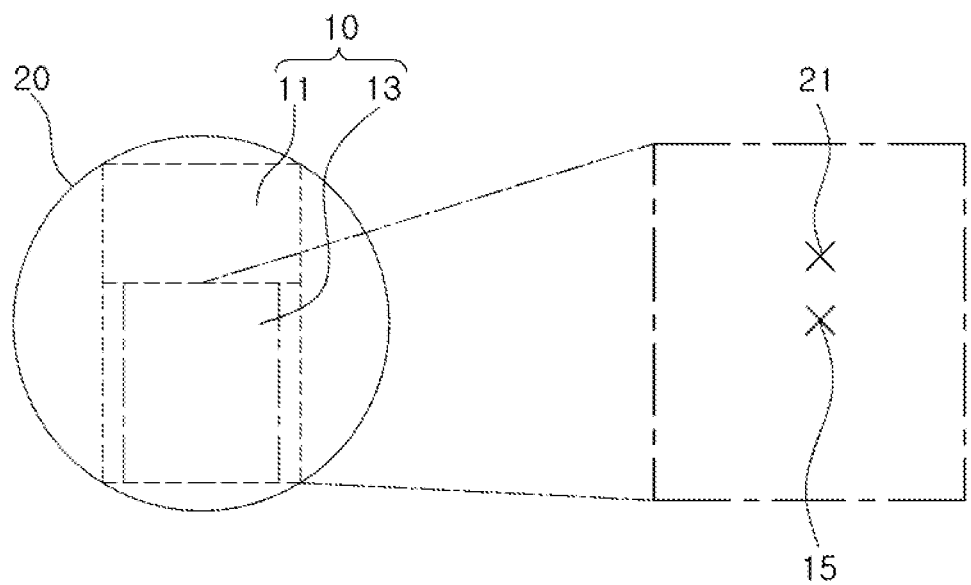
FIG. 9 is a reference drawing illustrating a dual lens module according to an example.

As illustrated in FIG. 9, in order for the camera module 1000 to perform imaging as a general camera module and imaging as an iris recognition camera module, an image sensor 10 is divided into an image sensor 11 for a general camera module and an image sensor 13 for an iris recognition camera module. The image sensor 11 for a general camera module and the image sensor 13 for an iris recognition camera module have geometric centers, respectively.

Here, the image sensor 10 extends lengthwise in one direction and is divided into the image sensor 11 for a general camera module and the image sensor 13 for an iris recognition camera module for use. The geometric center of each of the image sensor 11 for a general camera module and the image sensor 13 for an iris recognition camera module is offset from that of a lens 20, resulting in a reduction in quality of a captured image. For example, as illustrated in FIG. 9, a center 21 of the lens 20 and a center 15 of the image sensor 13 for an iris recognition camera module may be offset from each other.

Accordingly, a separate optical system, aligned with each of the center 21 of the image sensor 11 for a general camera module and the center 15 of the image sensor 13 for an iris recognition camera module, is used. This example utilizes an approximately '8'-shaped lens to provide first and second optical axes Z1 and Z2, illustrated in FIGS. 3 and 4. The first and second optical axes Z1 and Z2 are parallel to each other.

Figure 3A:
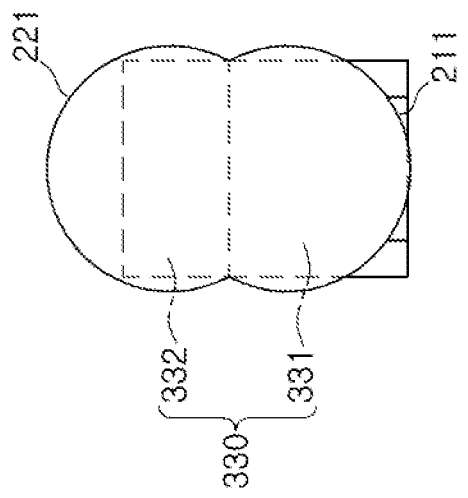
FIGS. 3A through 3C are plan views of dual lenses used in a camera module according to examples.
Figure 3B:
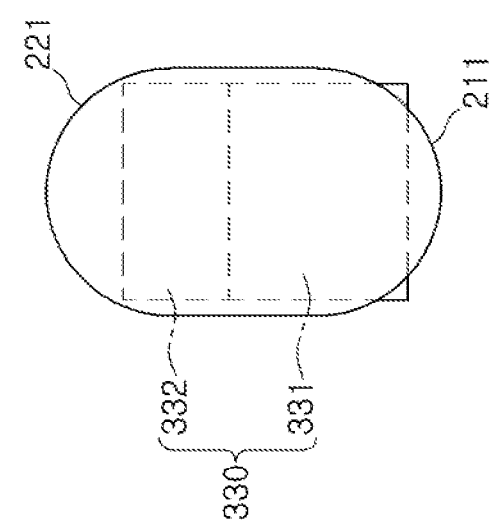
Figure 3C:
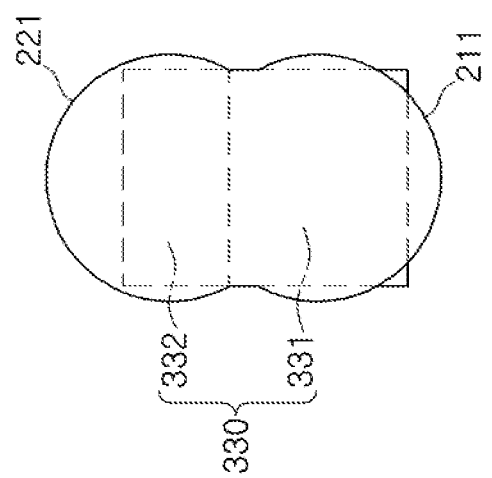
Figure 4:
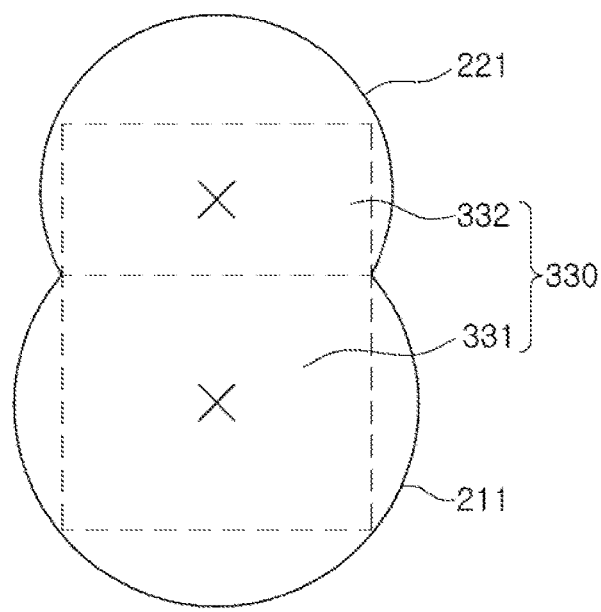
FIG. 4 is a plan view of a dual lens module used in a camera module according to another example.

Referring to FIGS. 3 and 4, a dual lens according to the example will be described. The dual lens includes first lens module 210 and second lens module 220. The first lens module 210 is used for general imaging, and the second lens module 220 is used for iris recognition imaging.

The first lens module 210 has a plurality of first lenses 211 stacked therein, and the second lens module 220 has a plurality of second lenses 221 stacked therein. The first and second lenses 211 and 221 have basically a circular shape, although other shapes are possible. A contact portion between first and second lenses 211 and 221 is provided in straight form such that the first and second lenses 211 and 221 are readily integrated with each other or adjacently parallel to each other. Accordingly, the dual lens, including the first and second lenses 211 and 221, may be '8'-shaped, as illustrated in FIGS. 3A through 4. The first and second lenses 211 and 221 are manufactured to be integrated with each other, or manufactured individually to be bonded or operable connected to each other.

As illustrated in FIGS. 3A through 3C, the second lens module 220 covers all image sensors 332 for an iris recognition camera module used for iris recognition imaging. An effective area of the first lens module 210, used for general imaging, is approximately the same as that of the second lens module 220.

In the case of FIG. 3A, the diameters of the effective areas of the first and second lenses 211 and 221 are approximately the same as each other. The first and second lenses 211 and 221 have an inwardly recessed region therebetween. The inwardly recessed region has a linear shape extending in a direction perpendicular to first or second optical axis Z1 or Z2.

In the case of FIG. 3B, the diameters of the effective areas of the first and second lenses 211 and 221 are approximately the same as each other. The first and second lenses 211 and 221 extend in a direction perpendicular to the first or second optical axis Z1 or Z2 from outermost sides of the first and second lenses 211 and 221, so as not to form an inwardly recessed region between the first and second lenses 211 and 221.

In the case of FIG. 3C, the diameters of the effective areas of the first and second lenses 211 and 221 are approximately the same as each other. The first and second lenses 211 and 221 have an inwardly recessed region therebetween. The inwardly recessed region has no straight line extending in the direction perpendicular to the first or second optical axis Z1 or Z2, and rounded portions of the first and second lenses 211 and 221 are in contact with each other.

As illustrated in FIG. 4, the entirety of an image sensor 331 for a general camera module, used for general imaging, is covered by the first lens module 210. The entirety of an image sensor 332 of the iris recognition camera module used for iris recognition imaging is covered by the second lens module 220. Accordingly, in one example the diameters of the effective areas of the first and second lenses 211 and 221 are different from each other.

The lens holder 200 is accommodated in the housing 100, and is movable inside the housing 100, in order to perform AF, zoom, and OIS functions. In an example, the housing 100 has an open upper portion and an open lower portion, and accommodates the lens holder 200 in an internal space thereof. The lens holder 200 is movable in optical axis directions of the first and second lens modules 210 and 220 in the housing 100, in order to focus. The housing 100 has the image sensor module 300 disposed therebelow.

The image sensor module 300 is provided as a device that converts light, incident in the lens holder 200, into an electrical signal. The image sensor module 300 includes an optical filter 310, an image sensor 330, and a printed circuit board (PCB) 350. The optical filter 310 performs both infrared blocking and infrared pass functions. In an example, a portion of the optical filter 310 filters infrared light from light incident in the lens holder 200, and the remainder of the optical filter 310 passes infrared light of the light incident in the lens holder 200.

The optical filter 310 is provided in the housing 100 so as to be disposed between the lens holder 200 and the image sensor 330. Also, when the optical filter 310 is disposed between the lens holder 200 and the image sensor 330, the optical filter 310 may be fixed to another member rather than the housing 100. The image sensor 330 converts light, incident in the lens holder 200, into an electrical signal. Also, the image sensor 330 generates an image, using a portion of the light incident in the lens holder 200, and recognizes one or both of the irises of a user, using the remainder of the light. The image sensor 330 is fixed to the PCB 350 and is electrically connected to the PCB 350 using wire bonding.

The camera module according to an example performs both general imaging and iris recognition imaging, using a single camera module. In an example, a portion of the optical filter 310 filters infrared light from light passing through the lens holder 200. Thus a portion of the image sensor 330, corresponding to the portion of optical filter 310, generates an image, using the light from which the infrared light has been filtered. Also, the remainder of optical filter 310 passes the infrared light from the light passing through lens holder 200. Therefore, a portion of image sensor 330, corresponding to the remainder of the optical filter 310, recognizes one or both of the irises of the user, using the infrared light. As a result, the camera module according to the example performs both general imaging and iris recognition imaging, using the single camera module, thereby enabling two-mode imaging, without requiring a camera module for general imaging and a separate camera module for iris recognition to be mounted in a portable electronic device.

Figure 5:
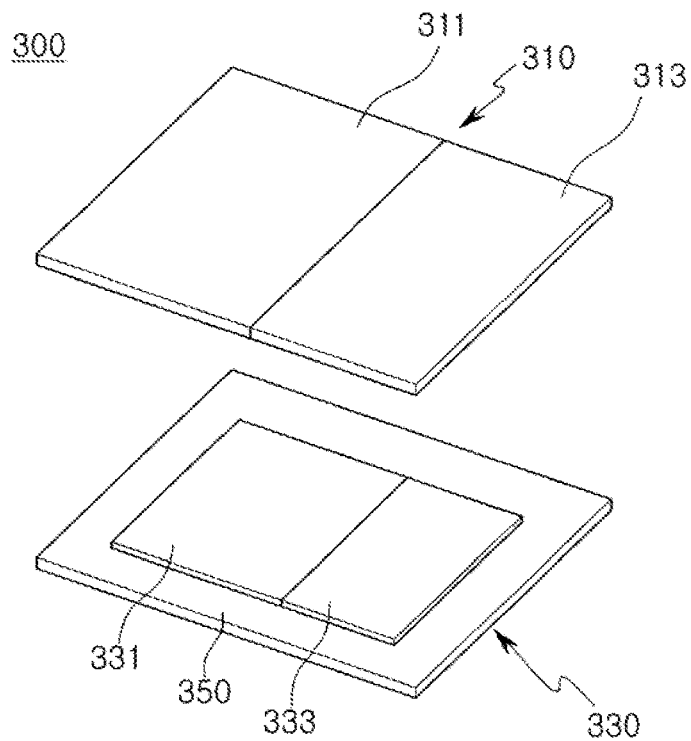
FIGS. 5 through 8 are diagrams of combinations of an optical filter and an image sensor according to examples.

FIG. 5 is a schematic perspective view of an image sensor module 300 according to a first example. Referring to FIG. 5, the image sensor module 300 includes the optical filter 310, the image sensor 330, and the PCB 350. The image sensor module 300 includes the optical filter 310 and the image sensor 330, each divided into two regions.

The optical filter 310 includes a first region 311 and a second region 313. In an example, the first region 311 is an infrared blocking filter blocking infrared light, and the second region 313 is an infrared pass filter passing infrared light. As illustrated in FIG. 2, the first region 311 is provided in a location in which the first lens module 210 is approximately coincident with the first region 311. The second region 313 is provided in a location in which the second lens module 220 is approximately coincident with the second region 313. The center of the first region 311 is approximately coincident with the first optical axis Z1 of the first lens module 210. The center of the second region 313 is approximately coincident with the second optical axis Z2 of the second lens module 220.

Also, the image sensor 330 includes a plurality of pixel arrays. In an example, the image sensor 330 includes a first pixel array 331 and a second pixel array 333. One of the first and second pixel arrays 331 and 333 is a color pixel array, and the other is a black-and-white pixel array. The color pixel array is provided in RGB format in the form of red, green, and blue. In the first example, the first pixel array 331 includes the color pixel array, and the second pixel array 333 includes the black-and-white pixel array.

Here, as illustrated in FIG. 2, the first pixel array 331 is provided in a location in which the first lens module 210 is approximately coincident with the first pixel array 331. The second pixel array 333 is provided in a location in which the second lens module 220 is approximately coincident with the second pixel array 333. The center of the first pixel array 331 is approximately coincident with the first optical axis Z1 of the first lens module 210. The center of the second pixel array 333 is approximately coincident with second optical axis Z2 of the second lens module 220. Thus, the first pixel array 331 performs general imaging, using visible light, and the second pixel array 333 performs iris recognition imaging, using infrared light. As a result, the image sensor module 300 performs both the general imaging and iris recognition imaging.

Figure 6:
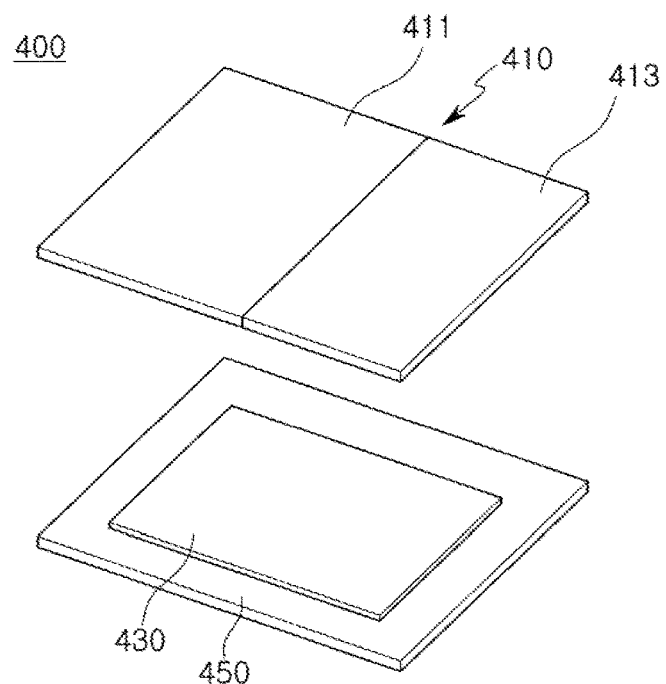

FIG. 6 is a schematic perspective view of an image sensor module 400 according to a second example. Referring to FIG. 6, the image sensor module 400 according to the second example includes an optical filter 410, an image sensor 430, and a PCB 450. The image sensor module 400 includes the optical filter 410 divided into two regions in the same manner as the image sensor module 300. Thus, a detailed description of the optical filter 410 will be omitted.

The image sensor 430 has only a single pixel array without being divided. In an example, a pixel array of the image sensor 430 is a color pixel array. In the image sensor module 400, the image sensor 430 performs both general imaging, using visible light, and iris recognition imaging, using infrared light, through the single pixel array (i.e., the color pixel array).

Figure 7:
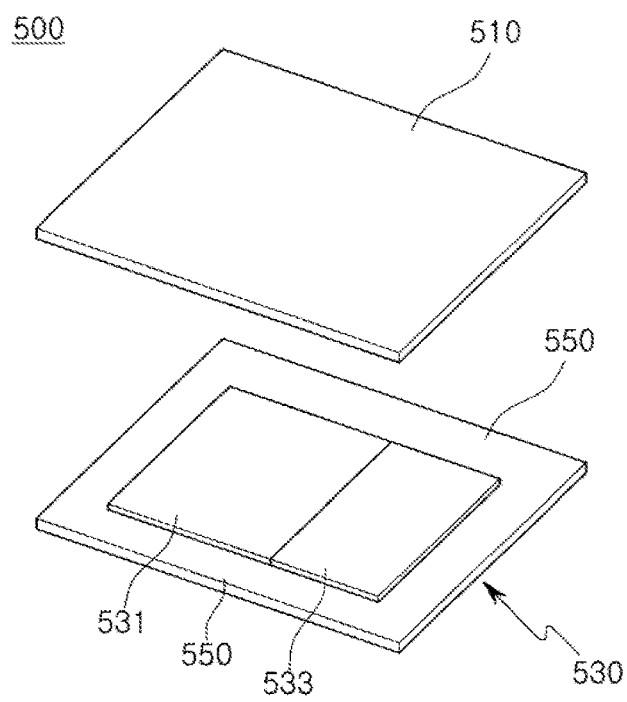

FIG. 7 is a schematic perspective view of an image sensor module 500 according to a third example. Referring to FIG. 7, the image sensor module 500 according to the third example includes an optical filter 510, an image sensor 530, and a PCB 550. The image sensor module 500 includes the image sensor 530 divided into two regions in the same manner as the image sensor module 300.

The image sensor 530 includes a plurality of pixel arrays. In an example, the image sensor 530 includes a first pixel array 531 and a second pixel array 533. A detailed configuration of the image sensor 530 is the same as the image sensor module 300, and thus a detailed description thereof will be omitted. Here, the optical filter 510 is a two-band pass filter that passes both visible light and infrared light of light passing through the lens holder 200, unlike in the optical filter 310 according to the first example.

Thus, the image sensor module 500 allows the optical filter 510 to pass both the visible light and infrared light, so that the first pixel array 531 of the image sensor 530 performs general imaging, using the visible light, and the second pixel array 533 of the image sensor 530 performs iris recognition imaging, using the infrared light. As a result, the image sensor module 500 according to the third example performs both general imaging and iris recognition imaging.

Figure 8:
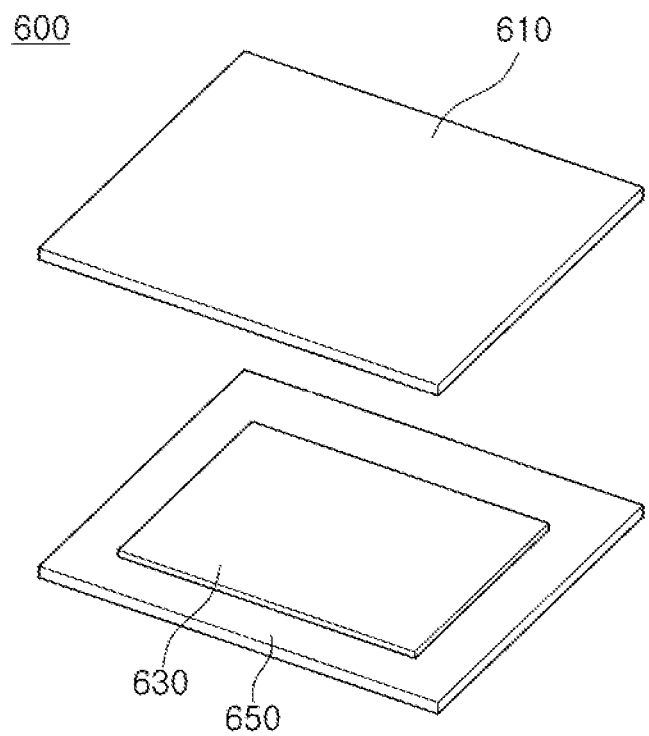

FIG. 8 is a schematic perspective view of an image sensor module 600 according to a fourth example. Referring to FIG. 8, the image sensor module 600 includes an optical filter 610, an image sensor 630, and a PCB 650. The optical filter 610 is a two-band pass filter that passes both visible light and infrared light of light passing through the lens holder 200, unlike in the optical filter 310.

The image sensor 630 has only a single pixel array, unlike in the image sensor 530 described above. In an example, the pixel array of the image sensor 530 is a color pixel array. Thus, the image sensor module 600 allows the optical filter 610 to pass both the visible light and infrared light. As a result, the image sensor 630 performs both general imaging, using the visible light, and iris recognition imaging, using the infrared light, through the single pixel array (i.e., the color pixel array).

According to the foregoing examples, the image sensor module according to an example and the camera module including the same perform both general imaging and iris recognition imaging, using the single camera module. Thus, the size of the portable electronic device, having the camera module mounted therein, is reduced.

As set forth above, according to the examples, an iris scanning camera module may perform both general imaging and iris recognition imaging, using a single camera module. Thus, the space, occupied by a camera module in a portable electronic device, may be reduced.

While this disclosure includes specific examples, it will be apparent after an understanding of the application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples.

Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An iris scanning camera module comprising:
a housing comprising an internal space;
a first lens module and a second lens module disposed in the internal space; and
an image sensor configured to convert light passing through the first lens module and the second lens module into an image,
wherein the image sensor comprises a first region comprising a color pixel array and a second region comprising a black-and-white pixel array,
wherein the color pixel array is aligned in a direction of an optical axis direction of the first lens module, and the black-and-white pixel array is aligned in a direction of an optical axis of the second lens module, and
wherein the optical axis of the first lens module is parallel to the optical axis of the second lens module.

2. The iris scanning camera module of claim 1, wherein the second lens module is configured to accommodate an iris recognition camera.

3. The iris scanning camera module of claim 2, wherein the optical axis of the second lens module is aligned with the center of the black-and-white pixel array.

4. The iris scanning camera module of claim 1, wherein the housing has an optical filter disposed between the image sensor and the first and second lens modules.

5. The iris scanning camera module of claim 4, wherein the optical filter comprises an infrared blocking filter region and an infrared pass filter region.

6. The iris scanning camera module of claim 5, wherein the infrared blocking filter region is aligned with the color pixel array of the image sensor, and the infrared pass filter region is aligned with the black-and-white pixel array of the image sensor.

7. The iris scanning camera module of claim 4, wherein the optical filter passes both infrared light and ultraviolet light.

8. The iris scanning camera module of claim 2, wherein the first lens module has a structure in which at least two lenses are stacked.

9. The iris scanning camera module of claim 8, wherein a number of stacked lenses of the first lens module is equal to or greater than a number of stacked lenses of the second lens module.

10. The iris scanning camera module of claim 1, wherein stacked lenses, provided in the first lens module and the second lens module, are integrated with each other or are separated from each other.

11. The iris scanning camera module of claim 10, wherein a diameter of an effective area of the first lens module is the same as a diameter of an effective area of the second lens module.

12. The iris scanning camera module of claim 10, wherein a diameter of the effective area of the first lens module is different from a diameter of the effective area of the second lens module.

13. A portable electronic device comprising:
   a body having a camera module according to claim 1 mounted therein.

14. The portable electronic device of claim 13, wherein the body has an infrared light source configured to emit infrared light.

15. The iris scanning camera module of claim 1, further comprising:
   a lens holder disposed in the internal space, wherein the first lens module and the second lens module are disposed inside the lens holder.

16. The iris scanning camera module of claim 1, wherein the image sensor is fixed to the housing and is configured to store the image.

17. The iris scanning module of claim 1, wherein first lenses of the first lens module, and second lenses of the second lens module are disposed in a contacted manner to form a figure "8" shape.

* * * * *